United States Patent [19]

Fujiwara et al.

[11] Patent Number: 5,753,681
[45] Date of Patent: May 19, 1998

[54] TREATMENT AND PROPHYLAXIS OF PANCREATITIS

[75] Inventors: Toshihiko Fujiwara, Ebina; Hiroyoshi Horikoshi, Funabashi; Masaharu Fukami, Yokohama, all of Japan

[73] Assignee: Sankyo Company, Limited, Tokyo, Japan

[21] Appl. No.: 819,686

[22] Filed: Mar. 17, 1997

[30] Foreign Application Priority Data

Mar. 18, 1996 [JP] Japan .................. 8-061063
Sep. 20, 1996 [JP] Japan .................. 8-250201

[51] Int. Cl.$^6$ .................. A61K 31/44; A61K 31/425
[52] U.S. Cl. .................. 514/337; 514/369; 514/370
[58] Field of Search .................. 514/337, 369, 514/370

[56] References Cited

U.S. PATENT DOCUMENTS

| | | | |
|---|---|---|---|
| 4,287,200 | 9/1981 | Kawamatsu et al. | 424/270 |
| 4,340,605 | 7/1982 | Kawamatsu et al. | 424/263 |
| 4,438,141 | 3/1984 | Kawamatsu et al. | 424/248.51 |
| 4,444,779 | 4/1984 | Kawamatsu et al. | 424/263 |
| 4,572,912 | 2/1986 | Yoshioka et al. | 514/369 |
| 4,687,777 | 8/1987 | Meguro et al. | 514/342 |
| 4,703,052 | 10/1987 | Eggler et al. | 514/337 |
| 4,725,610 | 2/1988 | Meguro et al. | 514/369 |
| 4,829,087 | 5/1989 | Ammon | 514/562 |
| 5,002,953 | 3/1991 | Hindley | 514/275 |
| 5,194,443 | 3/1993 | Hindley | 514/367 |
| 5,232,925 | 8/1993 | Hindley | 514/272 |
| 5,260,445 | 11/1993 | Hindley | 548/183 |

FOREIGN PATENT DOCUMENTS

| | | |
|---|---|---|
| 0 139 421 | 5/1985 | European Pat. Off. . |
| 0 332 332 | 9/1989 | European Pat. Off. . |
| 363589 | 4/1990 | European Pat. Off. . |
| 0 604 983 | 7/1994 | European Pat. Off. . |
| 0 676 398 | 10/1995 | European Pat. Off. . |
| 0 684 242 | 11/1995 | European Pat. Off. . |
| 0 708 098 | 4/1996 | European Pat. Off. . |
| 0 745 600 | 12/1996 | European Pat. Off. . |
| WO 95/02340 | 6/1985 | WIPO . |
| WO 95/35108 | 12/1995 | WIPO . |
| WO 95/35314 | 12/1995 | WIPO . |

OTHER PUBLICATIONS

Fujiwara et al, "Characterization of New Oral Antidiabetic Agent CS–045", Diabetes, vol. 37, Nov. 1988.

Hofmann et al, "New Oral Thiazolidinedione Antidiabetic Agents Act as Insulin Sensitizers", Diabetes Care, vol. 15, No. 8, Aug. 1992.

Ishii et al, "A Highly Potent Ghiazolidinedione Lacking Hematological and Cardiac Side–effects", Diabetes, 45, Suppl. 2, 141A (1996).

Bennett et al, "Alkylation of DNA in Rat Tissues following Administration of Streptozotocin", Cancer Research, 41, 2786–2790, Jul. 1981.

Tsuchitani et al, "A new diabetic strain of rat (WBN/Kob)", Laboratory Animals, 19(3), 200–207 (1985).

*Primary Examiner*—Kimberly Jordan
*Attorney, Agent, or Firm*—Frishauf, Holtz, Goodman, Langer & Chick, P.C.

[57] ABSTRACT

Insulin sensitizers, especially thiazolidinedione compounds, such as troglitazone, are useful for the treatment and prevention of pancreatitis.

52 Claims, No Drawings

TREATMENT AND PROPHYLAXIS OF PANCREATITIS

BACKGROUND OF THE INVENTION

The present invention relates to a new use for a series of known compounds, including thiazolidinedione compounds, oxazolidinedione compounds, isoxazolidinedione compounds and oxadiazolidinedione compounds, in the treatment and prophylaxis of pancreatitis.

Pancreatitis is commonly classified roughly as either acute pancreatitis or chronic pancreatitis depending on whether or not the condition persists after removal of the etiological agent. Except where the context otherwise requires, the term "pancreatitis", as used herein, includes both acute pancreatitis and chronic pancreatitis.

Probably about 40% of cases of acute pancreatitis may be attributed to alcohol abuse. Other causes include idiopathic, cholelithiasis, overeating and traumatic origins. The top three causes account for 70 to 80% of this disease.

The number of patients suffering from chronic pancreatitis has been steadily increasing in recent years, approximately in line with an increase in alcoholic intake, although it is also associated with an increase in the intake of protein and fat. Chronic pancreatitis is a pathological state characterised by lowered exocrine function due to pancreatic dysfunction. In chronic pancreatitis, the destruction of pancreatic parenchyma begins at the pancreatic acinar cells and soon extends to the islets of Langerhans. The main cause of chronic pancreatitis is alcohol abuse, and other causes include cholelithiasis, acute pancreatitis and idiopathic origins (particularly frequent in females). Recently, the incidence of chronic pancreatitis due to the abuse of alcohol has been increasing.

The preferred treatment of acute pancreatitis includes internal medicinal preservative treatments, such as removal of the cause of the disease, protection of the pancreas, prevention of auto-digestion in the pancreas, control of pain, countermeasures against infection and nutrition control.

On the other hand, in order to treat chronic pancreatitis, it would be desirable to inhibit deterioration of the pathological state of the pancreas and to regenerate and restore the pancreatic tissue, but no such treatment is available.

Accordingly, symptomatic treatment is generally given both for acute pancreatitis and for chronic pancreatitis. Various drugs have been used for the medical treatment of pancreatitis, of which the most widely used are protease inhibitors. It is thought that protease inhibitors inhibit the action of trypsin, which accelerates auto-digestion in the pancreas. In addition, it has been reported that protease inhibitors promote regeneration of exocrine tissue in the pancreas. However, this evaluation is controversial. Many thiazolidinedione derivatives are known to enhance insulin activity and to improve the diabetic state [Fujiwara et al., Diabetes, 37, 1549, (1988)]. In particular, a class of thiazolidinedione derivatives included in the compounds known as "insulin sensitizers" has proven of considerable value [C. A. Hofmann et al., Diabetes Care, 15, 1075, (1922)]. However, there has been no previous report that thiazolidinedione derivatives could be used to treat pancreatitis.

We have now surprisingly discovered that the class of compounds now known as "insulin sensitizers", and which includes various thiazolidinedione compounds, oxazolidinedione compounds, isoxazolidinedione compounds and oxadiazolidinedione compounds, has the ability to treat and prevent pancreatitis.

BRIEF SUMMARY OF THE INVENTION

It is therefore an object of the present invention to provide a method for the treatment or prophylaxis of pancreatitis by administering to a mammal, which may be human, suffering from or susceptible to pancreatitis an effective dose of an insulin sensitizer sufficient to treat or inhibit pancreatitis.

Other objects and advantages will become apparent as the description proceeds.

DETAILED DESCRIPTION OF THE INVENTION

At present, the experimental evidence seems to us to suggest that the activity inhibiting or preventing pancreatitis arises from the mode of action of the insulin sensitizers, and so the chemical structure of the compounds is believed to be of less importance than their activities. Accordingly, any compound having insulin sensitizing activity may be used in the present invention.

The insulin sensitizer may also be referred to as an insulin resistance-improving agent, and was originally used for the prevention and/or treatment of diabetes. The term embraces a wide variety of compounds, typically thiazolidinedione compounds, oxazolidinedione compounds, isoxazolidinedione compounds and oxadiazolidinedione compounds.

One class of preferred insulin sensitizers for use in the method of the present invention are those thiazolidinedione compounds of formula (I):

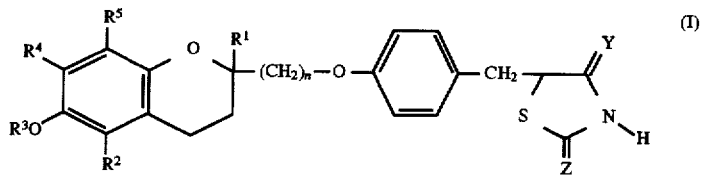

wherein:

$R^1$ and $R^2$ are the same as or different from each other and each represents a hydrogen atom or an alkyl group having from 1 to 5 carbon atoms;

$R^3$ represents a hydrogen atom, an aliphatic acyl group having from 1 to 6 carbon atoms, a cycloalkanecarbonyl group having from 5 to 7 carbon atoms in the cycloalkane part, a benzoyl group, a naphthoyl group, a benzoyl or naphthoyl group which is substituted by at least one substituent selected from the group consisting of substituents α, defined below, a heterocyclic acyl group in which the heterocyclic part has from 4 to 7 ring atoms of which from 1 to 3 are hetero-atoms selected from the group consisting of nitrogen, oxygen and sulfur atoms, a phenylacetyl group, a phenylpropionyl group, a phenylacetyl or phenylpropionyl group which is substituted by at least one halogen substituent, a cinnamoyl group, an alkoxycarbonyl group having from 1 to 6 carbon atoms in the alkoxy part or a benzyloxycarbonyl group;

$R^4$ and $R^5$ are the same as or different from each other and each represents a hydrogen atom, an alkyl group having from 1 to 5 carbon atoms or an alkoxy group having from 1 to 5 carbon atoms, or $R^4$ and $R^5$ together represent an alkylenedioxy group having from 1 to 4 carbon atoms;

n is 1, 2 or 3;

Y and Z are the same as or different from each other and each represents an oxygen atom or an imino group; and substituents α are selected from the group consisting of alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups having from 1 to 4 carbon atoms in each alkyl part, and nitro groups;

and pharmaceutically acceptable salts thereof.

In the compounds of formula (I) used in the present invention, where $R^1$ represents an alkyl group having from 1 to 5 carbon atoms, this may be a straight or branched chain alkyl group having from 1 to 5 carbon atoms, and examples include the methyl, ethyl, propyl, isopropyl, butyl, isobutyl, sec-butyl, t-butyl, pentyl and isopentyl groups, of which the methyl, ethyl, propyl, isopropyl, butyl, isobutyl and pentyl groups are preferred. Of these, those alkyl groups having from 1 to 4 carbon atoms are more preferred, and the methyl group is most preferred.

Where $R^2$ or $R^5$ represents an alkyl group having from 1 to 5 carbon atoms, this may be a straight or branched chain alkyl group having from 1 to 5 carbon atoms, and examples include the methyl, ethyl, propyl, isopropyl, butyl, isobutyl, sec-butyl, pentyl and isopentyl groups, of which the methyl, ethyl, propyl, isopropyl, butyl, isobutyl and pentyl groups are preferred. Of these, those alkyl groups having from 1 to 3 carbon atoms are more preferred, and the methyl group is most preferred.

Where $R^3$ represents an aliphatic acyl group, this may be a straight or branched chain group having from 1 to 6 carbon atoms, preferably an alkanoyl group having from 1 to 6 carbon atoms, for example a formyl, acetyl, propionyl, butyryl, isobutyryl, valeryl, isovaleryl, pivaloyl or hexanoyl group, of which the formyl, acetyl, propionyl, butyryl, isobutyryl, valeryl and hexanoyl groups are preferred. Those aliphatic acyl groups, particularly those alkanoyl groups, having from 1 to 4 carbon atoms are preferred and the acetyl group is most preferred.

Where $R^3$ represents an aromatic acyl group, this is a benzoyl or naphthoyl group in which the aromatic ring may be unsubstituted or it may be substituted by at least one substituent selected from the group consisting of substituents α, defined above and exemplified below. Examples of such substituents α include:

alkyl groups having from 1 to 4 carbon atoms, which may be straight or branched chain groups, such as the methyl, ethyl, propyl, isopropyl, butyl, isobutyl, sec-butyl and t-butyl groups, of which we prefer the methyl and t-butyl groups;

alkoxy groups having from 1 to 4 carbon atoms, which may be straight or branched chain groups, such as the methoxy, ethoxy, propoxy, isopropoxy, butoxy, isobutoxy, sec-butoxy and t-butoxy groups, of which we prefer the methoxy group;

halogen atoms, such as the fluorine, chlorine, bromine and iodine atoms, of which we prefer the fluorine and chlorine atoms;

hydroxy groups;

amino groups;

alkylamino groups having from 1 to 4 carbon atoms, which may be straight or branched chain groups, such as the methylamino, ethylamino, propylamino, isopropylamino, butylamino, isobutylamino, sec-butyl-amino, and t-butylamino groups, of which we prefer the methylamino group;

dialkylamino groups having from 1 to 4 carbon atoms in each alkyl part, which may be straight or branched chain groups, such as the dimethyl-amino, diethylamino, dipropylamino, diisopropylamino, dibutylamino, diisobutylamino, di-sec-butylamino, di-t-butylamino, N-methyl-N-ethylamino, N-methyl-N-propylamino, N-methyl-N-isopropylamino, N-methyl-N-butylamino, N-methyl-N-isobutylamino, N-methyl-N-sec-butylamino, N-methyl-N-t-butylamino, N-ethyl-N-propylamino, N-ethyl-N-isopropylamino, N-ethyl-N-butylamino, N-ethyl-N-isobutylamino, N-ethyl-N-sec-butylamino, N-ethyl-N-t-butylamino, N-propyl-N-isopropylamino, N-propyl-N-butylamino, N-propyl-N-isobutylamino, N-propyl-N-sec-butylamino, N-propyl-N-t-butylamino, N-isopropyl-N-butylamino, N-isopropyl-N-isobutylamino, N-isopropyl-N-sec-butylamino, N-isopropyl-N-t-butylamino, N-butyl-N-isobutyl-amino, N-butyl-N-sec-butylamino, N-butyl-N-t-butylamino, N-isobutyl-N-sec-butylamino, N-isobutyl-N-t-butylamino and N-sec-butyl-N-t-butylamino groups, of which we prefer the dimethylamino group; and nitro groups.

Where $R^3$ represents a substituted benzoyl or naphthoyl group, there is no particular restriction on the number of substituents, except such as may be imposed by the number of substitutable positions (5 in the case of benzoyl or 7 in the case of naphthoyl) and possibly by steric constraints. However, in general, we prefer from 1 to 3 substituents. Where there is more than one substituent, the substituents may be the same as or different from one another.

Examples of such substituted and unsubstituted benzoyl or naphthoyl groups include the benzoyl, 4-nitrobenzoyl, 3-fluorobenzoyl, 2-chlorobenzoyl, 3,4-dichlorobenzoyl, 4-aminobenzoyl, 3-dimethylaminobenzoyl, 2-methoxybenzoyl, 3,5-di-t-butyl-4-hydroxybenzoyl and 1- and 2-naphthoyl groups. Of these, we prefer the unsubstituted benzoyl and 1-naphthoyl groups, and most prefer the benzoyl group.

Where $R^3$ represents a cycloalkanecarbonyl group, this has from 5 to 7 carbon atoms in the cycloalkane ring, and thus a total of from 6 to 8 carbon atoms in the whole group. Examples of such groups include the cyclopentanecarbonyl, cyclohexanecarbonyl and cycloheptanecarbonyl groups, of which the cyclohexanecarbonyl group is preferred.

Where $R^3$ represents a heterocyclic acyl group, this is a group in which a heterocyclic group is attached to a carbonyl group. The heterocyclic part has from 4 to 7 ring atoms, more preferably 5 or 6 ring atoms, of which from 1 to 3, more preferably 1 or 2 and most preferably 1, are heteroatoms selected from the group consisting of nitrogen, oxygen and sulfur atoms. Where there are 3 hetero-atoms in the heterocyclic group, these are preferably all nitrogen atoms or one or two are nitrogen atoms and, correspondingly, two or one are oxygen and/or sulfur atoms. The heterocyclic group is preferably aromatic. Examples of preferred heterocyclic acyl groups include the furoyl (more preferably 2-furoyl), thenoyl (more preferably 3-thenoyl), 3-pyridinecarbonyl (nicotinoyl) and 4-pyridinecarbonyl (isonicotinoyl) groups.

Where $R^3$ represents a phenylacetyl or phenylpropionyl group which is substituted, preferably on the phenyl group, by at least one halogen substituent, the halogen substituent may be a fluorine, chlorine, bromine or iodine atom, and there may be from 1 to 5 such halogen substituents, preferably from 1 to 3 halogen substituents, and more preferably 1 halogen substituent. Examples of such groups include the p-chlorophenylacetyl, p-fluorophenylacetyl, p-bromophenylacetyl, p-iodophenylacetyl, o-chlorophenylacetyl, o-fluorophenylacetyl, o-bromophenyl-acetyl, o-iodophenylacetyl, m-chlorophenylacetyl, m-fluorophenylacetyl, m-bromophenylacetyl, m-iodophenylacetyl, 2,4-dichlorophenylacetyl, 2,4-difluorophenylacetyl, 2,4-dibromophenylacetyl, 2,4-diiodophenylacetyl, 3-(p-chlorophenyl)propionyl, 3-(p-fluorophenyl)propionyl, 3-(p-bromophenyl)-propionyl, 3-(p-iodophenyl) propionyl, 3-(o-chlorophenyl)propionyl, 3-(o-fluoro-phenyl)propionyl, 3-(o-bromophenyl)propionyl, 3-(o-iodophenyl)propionyl, 3-(m-chlorophenyl)propionyl, 3-(m-fluorophenyl) propionyl, 3-(m-bromophenyl)-propionyl, 3-(m-iodophenyl)propionyl, 3-(2,4-dichlorophenyl)propionyl, 3-(2,4-difluorophenyl)propionyl, 3-(2,4-dibromophenyl) propionyl and 3-(2,4-diiodo-phenyl)propionyl groups, of which the p-chlorophenylacetyl group is most preferred.

Where $R^3$ represents an alkoxycarbonyl group, this may be a straight or branched chain alkoxycarbonyl group having from 1 to 6 carbon atoms in the alkoxy part, i.e. having a total of from 2 to 7 carbon atoms, such as the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl and hexyloxycarbonyl groups, of which we prefer those alkoxycarbonyl group having from 2 to 4 carbon atoms and most prefer the ethoxycarbonyl group.

Where $R^4$ represents an alkyl group, this may be a straight or branched chain alkyl group having from 1 to 5 carbon atoms, such as the methyl, ethyl, propyl, isopropyl, butyl, isobutyl, t-butyl and pentyl groups, of which we prefer those alkyl groups having from 1 to 4 carbon atoms, more preferably a methyl or t-butyl group, and most preferably a methyl group.

Where $R^4$ or $R^5$ represents an alkoxy group, this may be a straight or branched chain alkoxy group having from 1 to 5 carbon atoms, such as the methoxy, ethoxy, propoxy, isopropoxy, butoxy, isobutoxy, t-butoxy and pentyloxy groups, of which we prefer those alkoxy groups having from 1 to 4 carbon atoms, more preferably a methoxy or t-butoxy group, and most preferably a methoxy group.

Where $R^4$ and $R^5$ together represent an alkylenedioxy group, this has from 1 to 4 carbon atoms and examples include the methylenedioxy, ethylenedioxy, propylenedioxy, trimethylenedioxy and tetramethylenedioxy groups, of which the methylenedioxy and ethylenedioxy groups are preferred.

n is 1,2 or 3, but is preferably 1.

Y and Z are the same as or different from each other and each represents an oxygen atom or an imino group; however, both are preferably oxygen atoms.

Preferred compounds used in the present invention are those compounds of formula (Ia):

wherein:

$R^1$, $R^2$, $R^4$ and $R^5$ are the same as or different from each other and each represents a hydrogen atom or an alkyl group having from 1 to 5 carbon atoms; and $R^3$ represents a hydrogen atom, an aliphatic acyl group having from 1 to 6 carbon atoms, a benzoyl group, a naphthoyl group, a benzoyl or naphthoyl group which is substituted by at least one substituent selected from the group consisting of substituents α, defined below, or an alkoxycarbonyl group having from 1 to 6 carbon atoms in the alkoxy part;

substituents α are selected from the group consisting of alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups having from 1 to 4 carbon atoms in each alkyl part, and nitro groups;

and pharmaceutically acceptable salts thereof.

Preferred classes of compounds used in the present invention are those compounds of formula (I) or (Ia) and pharmaceutically acceptable salts thereof, in which:

(A) $R^1$ represents an alkyl group having from 1 to 4 carbon atoms.

(B) $R^2$ represents a hydrogen atom or an alkyl group having from 1 to 3 carbon atoms.

(C) $R^3$ represents a hydrogen atom, an aliphatic acyl group having from 1 to 4 carbon atoms, an unsubstituted benzoyl or naphthoyl group, or an alkoxycarbonyl group having from 2 to 4 carbon atoms.

(D) $R^4$ represents an alkyl group having from 1 to 4 carbon atoms.

(E) $R^5$ represents a hydrogen atom or an alkyl group having from 1 to 3 carbon atoms.

In particular, of the above compounds, we prefer those compounds of formula (I) and (Ia), in which $R^1$ is as defined in (A) above, $R^2$ is as defined in (B) above, $R^3$ is as defined in (C) above, $R^4$ is as defined in (D) above, and $R^5$ is as defined in (E) above.

More preferred classes of compounds used in the present invention are those compounds of formula (I) and (Ia) and pharmaceutically acceptable salts thereof, in which:

(F) $R^1$ represents an alkyl group having from 1 to 4 carbon atoms.

(G) $R^2$ represents a hydrogen atom or an alkyl group having from 1 to 3 carbon atoms.

(H) $R^3$ represents a hydrogen atom, an acetyl group, a benzoyl group or an ethoxycarbonyl group.

(I) $R^4$ represents an alkyl group having from 1 to 4 carbon atoms.

(J) $R^5$ represents a hydrogen atom or an alkyl group having from 1 to 3 carbon atoms.

In particular, of the above compounds, we prefer those compounds of formula (I) and (Ia), in which $R^1$ is as defined in (F) above, $R^2$ is as defined in (G) above, $R^3$ is as defined in (H) above, $R^4$ is as defined in (I) above, and $R^5$ is as defined in (J) above.

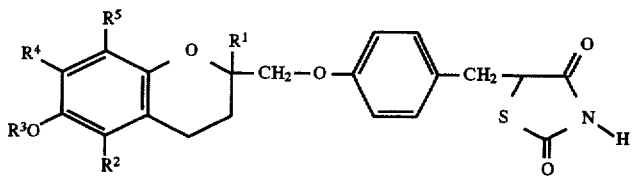

(Ia)

The most preferred classes of compounds used in the present invention are those compounds of formula (I) and (Ia) and pharmaceutically acceptable salts thereof, in which:

(K) $R^1$ represents a methyl group.
(L) $R^2$ represents a hydrogen atom or a methyl group.
(M) $R^3$ represents a hydrogen atom, an acetyl group or an ethoxycarbonyl group.
(N) $R^4$ represents a methyl or a t-butyl group.
(O) $R^5$ represents a hydrogen atom or a methyl group.

In particular, of the above compounds, we prefer those compounds of formula (I) and (Ia), in which $R^1$ is as defined in (K) above, $R^2$ is as defined in (L) above, $R^3$ is as defined in (M) above, $R^4$ is as defined in (N) above, and $R^5$ is as defined in (O) above.

When the compounds of formula (I) of the present invention contain at least one basic group in their molecules, they can thus form acid addition salts. Examples of such acid addition salts include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkanesulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid. Such acid addition salts may readily be prepared by conventional means.

The compounds of the present invention can also form salts with cations, e.g. metals. Examples of such salts include: salts with an alkali metal, such as sodium, potassium or lithium; salts with an alkaline earth metal, such as barium or calcium; salts with another metal, such as magnesium or aluminum; ammonium salts; organic base salts, such as a salt with methylamine, dimethylamine, triethylamine, diisopropylamine, cyclohexylamine or dicyclohexylamine; and salts with a basic amino acid, such as lysine or arginine. Such salts may likewise readily be prepared by conventional means.

The compounds of the present invention can exist in the form of various isomers.

Thus, the carbon atom at position 2 of the chromane ring and that at position 5 of the thiazolidine ring are both asymmetric carbon atoms. In each of the compounds of formula (I) and (Ia), stereoisomers due to these asymmetric carbon atoms as well as equimolar and non-equimolar mixtures thereof are all represented by only the one formula. Accordingly, the scope of the present invention covers all of these isomers separately, as well as all mixtures thereof.

In the compounds of formula (I) in which Y and Z both represent imino groups, in which Y and Z both represent oxygen atoms and in which one of Y and Z represents an oxygen atom and the other represents an imino group can exist in the form of various tautomers as explained in Japanese Patent Kokai Application Sho 60-51189, U.S. Pat. No. 4,572,912 and European Patent No. 139 421.

In each of the compounds of formula (I) and (Ia), the tautomers and equimolar and non-equimolar mixtures thereof are all represented by only the one formula. Accordingly, the scope of the present invention covers all of these tautomers and all mixtures thereof.

The compounds of the present invention can also form solvates (for example hydrates), and the present invention embraces all such solvates.

The present invention covers additionally all of the so-called "pro-drugs" which can be converted by metabolic change in vivo into any one of the compounds of formula (I) or salts thereof.

Specific examples of the compounds of formula (I) are those compounds of formula (Ia):

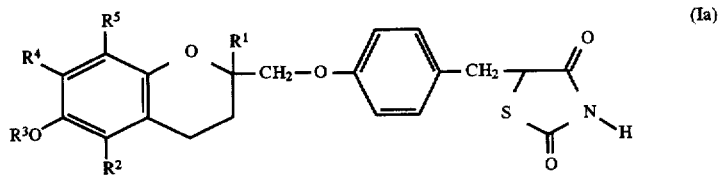

in which $R^1$, $R^2$, $R^3$, $R^4$ and $R^5$ are as defined in the following Table 1. In the Table, the following abbreviations are used:

| Ac: | acetyl, |
|---|---|
| iBu: | isobutyl, |
| tBu: | t-butyl, |
| Byr: | butyryl, |
| Bz: | benzoyl, |
| Etc: | ethoxycarbonyl, |
| Et: | ethyl, |
| Me: | methyl, |
| Pn: | pentyl. |

TABLE 1

| Compound No. | $R^1$ | $R^2$ | $R^3$ | $R^4$ | $R^5$ |
|---|---|---|---|---|---|
| 1 | Me | Me | H | Me | Me |
| 2 | H | Me | H | Me | Me |
| 3 | Me | H | H | H | H |
| 4 | Me | H | H | tBu | H |
| 5 | Et | Me | H | Me | Me |
| 6 | iBu | Me | H | Me | Me |
| 7 | Pn | Me | H | Me | Me |
| 8 | Me | Me | Ac | Me | Me |
| 9 | Me | Me | Bz | Me | Me |
| 10 | Me | Me | Etc | Me | Me |
| 11 | Me | H | Ac | Me | H |
| 12 | Me | H | H | Me | H |
| 13 | Me | Me | Byr | Me | Me |

Of the compounds listed above, preferred compounds are Compounds No.:

1. 5-[4-(6-Hydroxy-2,5,7,8-tetramethylchroman-2-ylmethoxy)benzyl]thiazolidine-2,4-dione;

4. 5-[4-(6-Hydroxy-2-methyl-7-t-butylchroman-2-ylmethoxy)benzyl]thiazolidine-2,4-dione;

5. 5-[4-(6-Hydroxy-2-ethyl-5,7,8-trimethylchroman-2-ylmethoxy)benzyl]-thiazolidine-2,4-dione;

6. 5-[4-(6-Hydroxy-2-isobutyl-5,7,8-trimethylchroman-2-ylmethoxy)benzyl]-thiazolidine-2,4-dione;

8. 5-[4-(6-Acetoxy-2,5,7,8-tetramethylchroman-2-ylmethoxy)benzyl]thiazolidine-2,4-dione;

10. 5-[4-(6-Ethoxycarbonyloxy-2,5,7,8-tetramethylchroman-2-ylmethoxy)benzyl]-thiazolidine-2,4-dione;

and pharmaceutically acceptable salts thereof.

More preferred compounds are Compounds No. 1, 4 and 10, and the most preferred compound is Compound No. 1 (commonly known as "troglitazone", by which name it is referred to hereafter).

The compounds of formula (I) and salts thereof of the present invention are known compounds, and are described in, for example, Japanese Patent Kokai Application Sho 60-51189, U.S. Pat. No. 4,572,912 and European Patent No. 0 139 421. They may be prepared as described in these documents or by other known methods.

In addition to the thiazolidine derivatives of formula (I) described above, we have found that other known insulin sensitizers can also be used for the treatment or prevention of pancreatitis, although the mechanism by which this is achieved is not known.

Examples of such other compounds include:

i. MCC-555: 5-[6-(2-Fluorobenzyloxy)-2-naphthyhnethyl] thiazolidine-2,4-dione, which is disclosed as an antilipemic and anti-diabetic agent in Diabetes, 45, Suppl. 2, 141A (1996) and Example 4 of EP 604 983A;

ii. Pioglitazone: 5-{4-[2-(5-Ethylpyridin-2-yl)ethoxy]benzyl}thiazolidine-2,4-dione, which is disclosed as an insulin sensitizer in Japanese Patent Publication No. Sho 62-42903 and No. Hei 5-66956 and in U.S. Pat. Nos. 4,287,200, 4,340,605, 4,438,141, 4,444,779 and 4,725,610;

iii. Englitazone: 5-(2-Benzyl-3,4-dihydro-2H-benzopyran-6-ylmethyl)-thiazolidine-2,4-dione, which is disclosed as an insulin sensitizer in Japanese Patent Publication No. Hei 5-86953 and in U.S. Pat. No. 4,703,052;

iv. BRL-49653: 5-[4-{2-[N-Methyl-N-(pyridin-2-yl)amino]ethoxy}benzyl]-thiazolidine-2,4-dione, which is disclosed as an insulin sensitizer in Japanese Patent Kokai Application No. Hei 1-131169 and in U.S. Pat. Nos. 5,002,953, 5,194,443, 5,232,925 and 5,260,445;

v. Compound A: 5-(4-{2-[1-(4-2'-pyridylphenyl)ethylideneaminooxy]ethoxy}-benzyl)thiazolidine-2,4-dione, which is disclosed as an insulin sensitizer in European Patent No. 708 098A;

vi. Compound B: 4-{4-[2-(5-Methyl-2-phenyloxazol-4-yl)ethoxy]benzyl}-isoxazolidine-3,5-dione, which is disclosed as an antilipemic and anti-diabetic agent in WO 95/18125;

vii. Compound C: 5-{4-(5-Methoxy-3- methylimidazo[4,5-b]pyridin-2-yl-methoxy)benzyl}thiazolidine-2,4-dione (and its hydrochloride), which are disclosed as insulin sensitizers in Japanese Patent Kokai Application No. Hei 7-330728 and in European Patent No. 676 398A;

viii. 5-[4-(6-Methoxy-1-methylbenzimidazol-2-ylmethoxy)benzyl]thiazolidine-2,4-dione, which is disclosed as an insulin sensitizer in European Patent No. 745 600A;

ix. 5-[4-(1-Methylbenzimidazol-2-ylnethoxy)benzyl] thiazolidine-2,4-dione, which is disclosed as an insulin sensitizer in European Patent No. 745 600A;

x. 5-[4-(5-Hydroxy-1,4,6,7-tetramethylbenzimidazol-2-ylmethoxy)benzyl]-thiazolidine-2,4-dione, which is disclosed as an insulin sensitizer in European Patent No. 745 600A;

xi. 5-[4-(1-Methylindolin-2-ylmethoxy)benzyl] thiazolidine-2,4-dione, which is disclosed as an insulin sensitizer in Japanese Patent Kokai Application No. Hei 7-330728 and in European Patent No. 676 398A;

xii. Darglitazone: 5-{4-[3-(5-methyl-2-phenyloxazol-4-yl)propionyl]benzyl}-thiazolidine-2,4-dione, which is disclosed as a hypoglycemic and hypocholesterolemic agent in Japanese Patent Kokai Application No. Hei 1-272574 and in European Patent No. 332 332A.

The compounds employed in the present invention can be administered by various routes. The route of administration is not particularly critical to the present invention, and is determined according to the form of the drug preparation, and the age, sex and condition of the patient, as well as the nature and degree of the disease. For example, for oral administration, the compounds may be administered in the form of tablets, pills, powders, granules, syrups, liquid preparations, suspensions, emulsions or capsules. Injections may be given intravenously by themselves or in admixture with the usual fluid replacements, such as glucose and amino acids; or they may, if necessary, be administered intramuscularly, intracutaneously, subcutaneously or intraperitoneally by themselves. When suppositories are used, these may be administered intrarectally.

The compounds of the present invention may be administered alone or in admixture with any known additives commonly used in the field of drug preparation such as vehicles, binders, disintegrators, lubricants, solubilizers, corrigents and coating agents. Such preparations may be obtained by known means.

When tablets are to be prepared, carriers which are widely known in this field can be employed, for example: vehicles, such as lactose, sucrose, sodium chloride, glucose, urea, starch, calcium carbonate, kaolin, crystalline cellulose and silicic acid; binders, such as water, ethanol, propanol, simple syrup, glucose solution, starch solution, gelatin solution, carboxymethyl cellulose, purified shellac, methyl cellulose, potassium phosphate and polyvinylpyrrolidone; disintegrators, such as dry starch, sodium alginate, agar powder, laminaran powder, sodium bicarbonate, calcium carbonate, polyoxyethylene sorbitan fatty acid esters, sodium laurylsulfate, stearic acid monoglyceride, starch and lactose; disintegration inhibitors, such as sucrose, stearine, cacao oil and hydrogenated oil; absorption accelerators, such as quaternary ammonium bases and sodium laurylsulfate; humectants, such as glycerin and starch; adsorbers, such as starch, lactose, kaolin, bentonite and colloidal silicic acid; and lubricants, such as purified talc, salts of stearic acid, powdery boric acid and polyethylene glycol. In addition, the tablets can, if necessary, be prepared as ordinary coated tablets, such as sugar-coated tablets, gelatin-coated tablets, enteric coated tablets, film-coated tablets, or as double-layer tablets or multi-layer tablets.

When pills are to be prepared, carriers which are widely known in this field can be employed, for example: vehicles, such as glucose, lactose, starch, cacao oil, hardened vegetable oil, kaolin and talc; binders, such as gum arabic, tragacanth powder, gelatin and ethanol; and disintegrators, such as laminaran agar.

When suppositories are to be prepared, carriers which are widely known in this field can be employed, for example: polyethylene glycol, cacao oil, higher alcohols, higher alcohol esters, gelatin and semi-synthetic glycerides.

When injections are to be prepared, they may be solutions, emulsions or suspensions which are preferably sterilised and isotonic to blood. When these solutions, emulsions and suspensions are to be prepared, diluents conventionally used in this field can be employed; for example, water, ethyl alcohol, propylene glycol, ethoxy-isostearyl alcohol, polyoxy-isostearyl alcohol and fatty acid esters of polyoxyethylene sorbitan. In this case, sufficient sodium chloride, glucose or glycerin to make the solution isotonic may be included in these preparations; or ordinary solubilizers, buffers or pain suppressers may be added.

In addition, coloring agents, preservatives, perfumes, flavors, sweetening agents and any other drugs may be added, if necessary.

The amount of the active ingredient contained in these preparations is not particularly critical, and may be selected over a wide range. In general, from 1 to 70% by weight, preferably from 1 to 30% by weight, of the active ingredient may be present in the whole composition.

Although the dosage may vary depending on the symptoms, age and body weight of the patient, as well as the route of administration and the form of the drug, an upper limit of 5,000 mg (preferably 1,000 mg, and more preferably 500 mg), and a lower limit of 0.5 mg (preferably 10 mg, and more preferably 50 mg), may preferably be given daily to an adult human patient.

BIOLOGICAL ACTIVITY

Since the decrease in the amount of pancreatic parenchyma resulting from chronic pancreatitis causes loss of pancreatic weight, any suppression of the decrease in the amount of pancreatic parenchyma can be used as an index for evaluating any improvement in the pancreatitis. Furthermore, since degeneration and necrosis of the pancreatic parenchyma and its replacement by connective tissue occurs in chronic pancreatitis, the seriousness of the pancreatitis can be estimated by histopathologically measuring the area over which the pancreatic parenchyma is replaced with connective tissue (known as the "cicatrized area").

Measurement of the weight of the pancreas may be carried out by conventional procedures after the experimental animals have been sacrificed by phlebotomy.

In pancreatitis, secretion of digestive enzymes is impaired and delivery of digestive enzymes to the duodenum is reduced. In addition, digestive enzymes leak into the blood and their level in the blood and urine increase. Accordingly, the extent of pancreatitis can be estimated by measuring the amount of digestive enzymes which have leaked into the blood (Methods of Clinical Examination: Kinbara Publisher).

EXAMPLES

The invention is further illustrated by the following Examples, which illustrate the biological activities of the compounds of the present invention, and the subsequent Preparation, which illustrates the preparation of compositions of the present invention.

The following general procedure may be used to test a compound to determine if it is effective against pancreatitis.

The effects of pancreatitis may be simulated, as is conventional, in experimental animals, by the administration of streptozotocin [(N-methylnitroso-carbamoyl)-D-glucosamine: R. A. Bennett et al., Cancer Res., 41, 2786–2790, (1981); a product of Sigma Chemical Company], which is capable of specifically destroying the Langerhans islet B cells and which thus induces a decrease in pancreatic weight. Streptozotocin is administered intravenously to the experimental animal, and then a powdered feed admixed with a test compound is given to a group of animals which have been dosed with streptozotocin. This group is hereafter referred to as the "treated group". Meanwhile, a powdered feed only is given to another group of animals which have been dosed with streptozotocin. This group is hereafter referred to as the "control group". Normal animals (undosed) fed with the feed only are also used as a blank group against the experimental animals (dosed with streptozotocin). After the test compounds have been administered to the animals for a predetermined period, each animal is sacrificed to measure its pancreatic weight.

The measurement of the cicatrized area may also be carried out by conventional procedures. More specifically, male WBN/Kob rats are used as models of spontaneous chronic pancreatitis and are fed with a powdered feed admixed with a test compound. The pancreas of each animal is then totally enucleated. Its weight is measured and also the cicatrized area is measured relative to the total cross-sectional area of the pancreas tissue sliced by an image analyser.

The measurement of digestive enzymes may also be carried out by conventional procedures. For example, after the test drug mixed into powdered feed has been administered to male WBN/Kob rats for a definite period, the blood may be collected and the lipase activity (one of the digestive enzymes) in the plasma may be measured.

EXAMPLE 1

Pancreatic Weight Loss Inhibitory Effect (i) Effect of Streptozotocin

The test animals were Wistar-Imamichi rats each having a body weight of about 200 g and employed in groups of rats each consisting of 5 animals. Each test animal was administered streptozotocin intravenously at a dose of 20 mg/kg or 40 mg/kg. After seven days, the rats were sacrificed, and the pancreas of each animal was weighed.

The results are summarised in Table 2.

TABLE 2

| Streptozotocin (mg/kg) | Pancreatic weight (mg/kg) |
|---|---|
| 0 | 991 ± 18 |
| 20 | 984 ± 30 |
| 40 | 958 ± 25 |

As can be clearly seen from Table 2, the administration of streptozotocin caused the pancreatic weight to decrease.

(ii) Inhibitory Effect

The test animals were Wistar-Imamichi rats each having a body weight of about 200 g and employed in groups of rats each consisting of 12 animals. Streptozotocin was administered intravenously at a dose of 25 mg/kg once to each animal. 7 days after the administration, a group of rats was fed with a powdered feed F2 (Funabashi Farms) admixed with 0.2% of troglitazone {5-[4-(6-hydroxy-2,5,7,8-tetramethylchroman-2-ylmethoxy)benzyl]thiazolidine-2,4-dione}, and this continued for 14 days. The average dose of the compound during this period was 170 mg/kg/day. This group is hereinafter referred to as "the treated group".

Meanwhile, another group of rats was fed with the powdered feed F2 only. This group is hereinafter referred to as "the control group". On the other hand, as a blank group against the experimental animals to which streptozotocin was administered, rats undosed with streptozotocin were fed with the powdered feed F2 only. This group is hereinafter referred to as "the normal group". After a predetermined period, the rats were sacrificed and the pancreatic weight of each animal was measured.

The results are summarised in Table 3.

TABLE 3

| Group | Pancreatic weight (mg) |
|---|---|
| Normal group | 1333 ± 43 |
| Control group | 1253 ± 39 |
| Treated group | 1435 ± 40* |

*$p < 0.05$ vs. control group

As can be clearly seen from Table 3, troglitazone significantly inhibited the pancreatic weight loss caused by the administration of streptozotocin. 97 to 98% of the pancreas consisted of exocrine pancreatic tissue, and there were observed no lesions such as edema. Accordingly, the increase in pancreatic weight is thought to be attributable to the increase in the exocrine pancreatic tissue achieved by the administration of troglitazone.

EXAMPLE 2

Increase in the Pancreatic Weight

The test animals were male WBN/Kob rats, which are commonly used as models of spontaneous chronic pancreatitis and suffer pancreatic weight loss and dysfunction of the exocrine pancreatic tissue due to degeneration and necrosis of the pancreatic parenchyma and its replacement by connective tissue [Tsuchitani et al., Laboratory Animals, 19(3), 200–207, (1985)]. Each group of test animals contained 4 animals, and the animals were used for the experiment when they had reached 12 weeks old. The animals were fed with powdered feed F2 mixed with 0.2% of troglitazone for three months. This group is hereinafter referred to as "the treated group". The average dose of the compound during this period was 140 mg/kg/day. Meanwhile, another four rats (control group) were fed with the powdered feed F2 only. After the rats had been fed with the feeds for three months, the pancreas of each animal was totally enucleated and its weight was measured. The results are summarised in Table 4.

TABLE 4

| Test group | Pancreatic weight (mg) |
| --- | --- |
| Control group | 773 ± 17 |
| Treated group | 936 ± 27** |

**p < 0.01 vs. control group

It can be seen from the above results that the pancreatic weight of the treated group showed a significant increase compared with that of the control group. Since 97 to 98% of the pancreas consists of exocrine pancreatic tissue, it is considered that the increase in the pancreatic weight results from an increase in the exocrine pancreatic tissue.

EXAMPLE 3

Suppression of the Decrease in the Pancreatic Weight

The procedure described in Example 2 was repeated, except that the test compound was pioglitazone ("the pioglitazone group"), BRL-49653 ("the BRL-49653 group"), or Compound A ("the Compound A group"). The results are shown in the following Table 5, which also shows the number of animals in each group and the dose of each test compound.

TABLE 5

| Test group | Number in group | Dose (%) | Average dose (mg/kg/day) | Pancreatic weight (mg) |
| --- | --- | --- | --- | --- |
| †Normal group | 4 | — | — | 1152 ± 43 |
| Control group | 5 | — | — | 680 ± 26 |
| Pioglitazone group | 5 | 0.05 | 25 | 982 ± 52*** |
| BRL-49653 group | 5 | 0.005 | 2.5 | 976 ± 51*** |

TABLE 5-continued

| Test group | Number in group | Dose (%) | Average dose (mg/kg/day) | Pancreatic weight (mg) |
| --- | --- | --- | --- | --- |
| Compound A group | 5 | 0.005 | 3.0 | 853 ± 44** |

†age matched Wistar rats
*p < 0.001, p < 0.01 vs. control group

It can be seen from the above results that the decrease in pancreatic weight was significantly suppressed in each of the treated groups compared with the control group. Since 97 to 98% of the pancreas consists of exocrine pancreatic tissue, it is thought that the increase in pancreatic weight results from an increase in the exocrine pancreatic tissue.

EXAMPLE 4

Cicatrized Area of Pancreatic Tissue

In order to evaluate the results of Example 2 histopathologically, each pancreas used for weight measurement in Example 2 was fixed in 10% neutral formalin. It was then divided into a spleen side half and a duodenum side half, and each half was sliced at 3 mm intervals to provide cross-sectional tissue pieces. All of these tissue pieces were subjected to paraffin sectioning by conventional procedures and then to hematoxylin-eosin staining and Masson's trichrome staining to prepare two tissue preparations, which were used for histopathological examination. The total cross-sectional area of the pancreatic tissue piece on each preparation was measured using an image analyser (SPICCAII, manufactured by Olympus Optical Co., Ltd.). The results are summarised in Table 6.

In addition, the surface area of the zone which had undergone degeneration and necrosis and in which the exocrine pancreatic tissue was replaced with connective tissue (the cicatrized area) was measured using an image analyser. The results are summarised in Table 7.

TABLE 6

| Total cross-sectional area of pancreatic tissue piece (mm²) | | |
| --- | --- | --- |
| Site | Control group | Treated group |
| Spleen side pancreatic half | 150.5 ± 4.6 | 172.6 ± 5.3* |
| Duodenum side half | 89.5 ± 6.6 | 132.8 ± 23.6 |

*p < 0.05 vs. Control group

It can be seen from the above results that the total cross-sectional area of the pancreatic tissue from the treated group showed a notable increase compared with that of the control group. In this measurement, since any change in the tissue which might have caused an increase in the pancreatic weight (such as edema) was not observed, it is thought that this result indicates an increase in the exocrine pancreatic tissue (i.e. simple hypertrophy).

TABLE 7

| Cicatrized area in the exocrine pancreatic tissue (mm²) | | |
| --- | --- | --- |
| Site | Control group | Treated group |
| Spleen side pancreatic half | 5.95 ± 0.90 | 3.31 ± 0.48* |
| Duodenum side half | 10.84 ± 0.60 | 6.76 ± 1.37* |

*p < 0.05 vs. control group

In this case, the treated group showed a significantly low value of the cicatrized area compared with the control group.

Accordingly, it can be concluded that degeneration and necrosis in the exocrine pancreatic tissue are suppressed in the treated group.

EXAMPLE 5

Cicatrized Area of Pancreatic Tissue

In order to evaluate the results of Example 3 histopathologically, the total cross-sectional area and cicatrized area of each pancreas whose weight was measured in Example 3 was measured by the procedure described in Example 4. The results are summarised in Tables 8 and 9, respectively.

TABLE 8

Total cross-sectional area of pancreatic tissue piece (mm$^2$)

| Test group | Spleen side pancreatic half | Duodenum side |
|---|---|---|
| Control group | 99.3 ± 9.8 | 90.3 ± 14.9 |
| Pioglitazone group | 157.8 ± 16.1** | 122.0 ± 9.8 |
| BRL-49653 group | 147.2 ± 14.2* | 100.9 ± 2.1 |
| Compound A group | 100.8 ± 12.5 | 90.3 ± 10.2 |

**$p < 0.01$, *$p < 0.05$ vs. Control group

TABLE 9

Cicatrized area in the exocrine pancreatic tissue (mm$^2$)

| Test group | Spleen side pancreatic half | Duodenum side |
|---|---|---|
| Control group | 8.11 ± 0.76 | 5.52 ± 0.86 |
| Pioglitazone group | 4.98 ± 1.03* | 1.12 ± 0.26** |
| BRL-49653 group | 5.40 ± 1.35 | 1.21 ± 0.40** |
| Compound A group | 2.62 ± 0.51** | 1.17 ± 0.15** |

**$p < 0.01$, *$p < 0.05$ vs. Control group

It can be seen from the above results (Table 8) that the total cross-sectional area of the pancreatic tissue from each of the groups using a test compound showed a notable increase compared with that of the control group. In this measurement, since no change in the tissue which might have caused an increase in pancreatic weight (such as edema) was observed, it is thought that this result indicates an increase in the exocrine pancreatic tissue (i.e. simple hypertrophy).

In addition, each of the groups using a test compound showed a significantly low value of the cicatrized area compared with the control group (Table 9). Accordingly, it can be concluded that degeneration and necrosis in the exocrine pancreatic tissue are suppressed in these groups.

EXAMPLE 6

Effect of Long Term Troglitazone Treatment on Plasma Lipase Activity and Increase in the Pancreatic Weight The test animals were male WBN/Kob rats. Each group of test animals contained 6 animals, and the animals were used for the experiment when they had reached 12 weeks old. The animals were fed with powdered feed F2 mixed with 0.2% or 0.05% of troglitazone for 9.5 months. These groups are hereinafter referred to as "the 0.2% group" and "the 0.05% group", respectively. The average doses of the compound during this period were 120 mg/kg/day and 30 mg/kg/day, respectively. Meanwhile, another six rats (control group) were fed with the powdered feed F2 only. After the rats had been fed with the feeds for 9.5 months, each rat was decapitated and its blood was collected. The blood serum was separated and the plasma lipase level was measured using an autoanalyser (type 7250, manufactured by Hitachi Ltd.). The plasma lipase activities of both the 0.2% group and the 0.05% group showed a significant decrease compared with that of the control group.

After the blood had been collected, the pancreas of each animal was totally enucleated and weighed. The pancreatic weight of both the 0.2% group and the 0.05% group showed a significant increase compared with that of the control group. The results are summarised in Table 10.

TABLE 10

| Test Group | Plasma Lipase Activity (IU/l) | Pancreatic Weight (mg) |
|---|---|---|
| Control group | 33.7 ± 7.8 | 804 ± 35 |
| 0.05% group | 17.5 ± 2.2 | 906 ± 63 |
| 0.2% group | 13.2 ± 1.0* | 1164 ± 52*** |

***$p < 0.001$, *$p < 0.05$ vs. control group

EXAMPLE 7

Cicatrized Area of Pancreatic Tissue

In order to evaluate the results of Example 6 histopathologically, the total cross-sectional area and cicatrized area of each pancreas whose weight was measured in Example 6 was measured by the procedure described in Example 4. The results are summarised in Tables 11 and 12, respectively.

TABLE 11

Total cross-sectional area of pancreatic tissue piece (mm$^2$)

| Test group | Spleen side pancreatic half | Duodenum side |
|---|---|---|
| Control group | 103.0 ± 16.9 | 106.1 ± 6.6 |
| 0.05% group | 96.2 ± 8.2 | 110.6 ± 7.7 |
| 0.2% group | 141.9 ± 10.6* | 122.3 ± 7.4 |

*$p < 0.05$ vs. Control group

TABLE 12

Cicatrized area in the exocrine pancreatic tissue (mm$^2$)

| Test group | Spleen side pancreatic half | Duodenum side |
|---|---|---|
| Control group | 4.96 ± 0.82 | 2.48 ± 0.39 |
| 0.05% group | 1.68 ± 0.12** | 1.03 ± 0.16** |
| 0.2% group | 1.23 ± 0.19** | 0.65 ± 0.06** |

**$p < 0.01$ vs. Control group

It can be seen from the above results (Table 11) that the total cross-sectional area of the pancreatic tissue from each of the groups using a test compound showed a notable increase compared with that of the control group. In this measurement, since no change in the tissue which might have caused an increase in pancreatic weight (such as edema) was observed, it is thought that this result indicates an increase in the exocrine pancreatic tissue (i.e. simple hypertrophy).

In addition, each of the groups using a test compound showed a significantly low value of the cicatrized area compared with the control group (Table 12). Accordingly, it can be concluded that degeneration and necrosis in the exocrine pancreatic tissue are suppressed in these groups.

EXAMPLE 8

Acute Toxicity

Acute toxicity was assayed by conventional procedures. More specifically, troglitazone was orally administered to three ddY mice (male) in a single dose of 300 mg/kg, and the mice were observed for 5 days. At the end of this time, the animals were all alive. When the acute toxicities of Compounds No. 2, 3, 4 and 10 were measured in the same manner, the mice were all alive after an oral dose of 300 mg/kg or more.

| Capsules | |
|---|---|
| Troglitazone | 100 mg |
| Lactose | 168.3 mg |
| Corn starch | 70 mg |
| Magnesium stearate | 1.7 mg |
| Total volume | 340.0 mg |

The powders of the above formulation were mixed and passed through a 20-mesh sieve (tyler standard mesh), and the resulting mixed powder was packed in gelatin capsules to prepare capsules.

We claim:

1. A method for the treatment or prophylaxis of pancreatitis by administering to a human suffering from or susceptible to pancreatitis an effective dose of an insulin sensitizer sufficient to treat or inhibit pancreatitis.

2. The method of claim 1, wherein said insulin sensitizer is selected from the group consisting of thiazolidinedione compounds, oxazolidinedione compounds, isoxazolidinedione compounds and oxadiazolidinedione compounds.

3. The method of claim 1, wherein said insulin sensitizer is selected from the group consisting of thiazolidinedione compounds and isoxazolidinedione compounds.

4. The method of claim 1, wherein said insulin sensitizer is selected from the group consisting of compounds of formula (I):

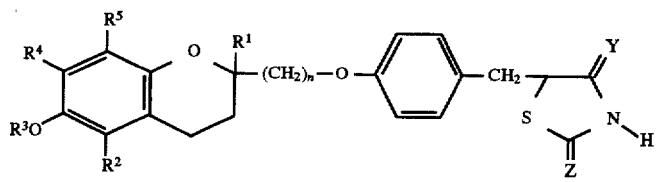

wherein:

$R^1$ and $R^2$ are the same as or different from each other and each represents a hydrogen atom or an alkyl group having from 1 to 5 carbon atoms;

$R^3$ represents a hydrogen atom, an aliphatic acyl group having from 1 to 6 carbon atoms, a cycloalkanecarbonyl group having from 5 to 7 carbon atoms in the cycloalkane part, a benzoyl group, a naphthoyl group, a benzoyl or naphthoyl group which is substituted by at least one substituent selected from the group consisting of substituents α, defined below, a heterocyclic acyl group in which the heterocyclic part has from 4 to 7 ring atoms of which from 1 to 3 are hetero-atoms selected from the group consisting of nitrogen, oxygen and sulfur atoms, a phenylacetyl group, a phenylpropionyl group, a phenylacetyl or phenylpropionyl group which is substituted by at least one halogen substituent, a cinnamoyl group, an alkoxycarbonyl group having from 1 to 6 carbon atoms in the alkoxy part or a benzyloxycarbonyl group;

$R^4$ and $R^5$ are the same as or different from each other and each represents a hydrogen atom, an alkyl group having from 1 to 5 carbon atoms or an alkoxy group having from 1 to 5 carbon atoms, or $R^4$ and $R^5$ together represent an alkylenedioxy group having from 1 to 4 carbon atoms;

n is 1,2or3;

Y and Z are the same as or different from each other and each represents an oxygen atom or an imino group; and substituents α are selected from the group consisting of alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups having from 1 to 4 carbon atoms in each alkyl part, and nitro groups;

and pharmaceutically acceptable salts thereof.

5. The method of claim 4, wherein said insulin sensitizer is selected from the group consisting of compounds of formula (Ia):

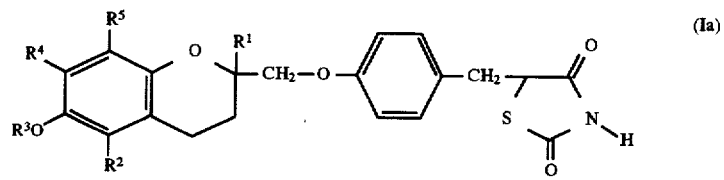

wherein:

$R^1$, $R^2$, $R^4$ and $R^5$ are the same as or different from each other and each represents a hydrogen atom or an alkyl group having from 1 to 5 carbon atoms; and $R^3$ represents a hydrogen atom, an aliphatic acyl group having from 1 to 6 carbon atoms, a benzoyl group, a naphthoyl group, a benzoyl or naphthoyl group which is substituted by at least one substituent selected from the group consisting of substituents α, defined below, or an alkoxycarbonyl group having from 1 to 6 carbon atoms in the alkoxy part;

substituents α are selected from the group consisting of alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups having from 1 to 4 carbon atoms in each alkyl part, and nitro groups;

and pharmaceutically acceptable salts thereof.

6. The method of claim 4, wherein $R^1$ represents an alkyl group having from 1 to 4 carbon atoms.

7. The method of claim 4, wherein $R^2$ represents a hydrogen atom or an alkyl group having from 1 to 3 carbon atoms.

8. The method of claim 4, wherein $R^3$ represents a hydrogen atom, an aliphatic acyl group having from 1 to 4 carbon atoms, an unsubstituted benzoyl or naphthoyl group, or an alkoxycarbonyl group having from 2 to 4 carbon atoms.

9. The method of claim 4, wherein $R^4$ represents an alkyl group having from 1 to 4 carbon atoms.

10. The method of claim 4, wherein $R^5$ represents a hydrogen atom or an alkyl group having from 1 to 3 carbon atoms.

11. The method of claim 4, wherein:

$R^1$ represents an alkyl group having from 1 to 4 carbon atoms;

$R^2$ represents a hydrogen atom or an alkyl group having from 1 to 3 carbon atoms;

$R^3$ represents a hydrogen atom, an aliphatic acyl group having from 1 to 4 carbon atoms, an unsubstituted benzoyl or naphthoyl group, or an alkoxycarbonyl group having from 2 to 4 carbon atoms;

$R^4$ represents an alkyl group having from 1 to 4 carbon atoms; and $R^5$ represents a hydrogen atom or an alkyl group having from 1 to 3 carbon atoms.

12. The method of claim 4, wherein $R^3$ represents a hydrogen atom, an acetyl group, a benzoyl group or an ethoxycarbonyl group.

13. The method of claim 4, wherein:

$R^1$ represents an alkyl group having from 1 to 4 carbon atoms;

$R^2$ represents a hydrogen atom or an alkyl group having from 1 to 3 carbon atoms;

$R^3$ represents a hydrogen atom, an acetyl group, a benzoyl group or an ethoxycarbonyl group;

$R^4$ represents an alkyl group having from 1 to 4 carbon atoms; and $R^5$ represents a hydrogen atom or an alkyl group having from 1 to 3 carbon atoms.

14. The method of claim 4, wherein $R^1$ represents a methyl group.

15. The method of claim 4, wherein $R^2$ represents a hydrogen atom or a methyl group.

16. The method of claim 4, wherein $R^3$ represents a hydrogen atom, an acetyl group or an ethoxycarbonyl group.

17. The method of claim 4, wherein $R^4$ represents a methyl or a t-butyl group.

18. The method of claim 4, wherein $R^5$ represents a hydrogen atom or a methyl group.

19. The method of claim 4, wherein:

$R^1$ represents a methyl group;

$R^2$ represents a hydrogen atom or a methyl group;

$R^3$ represents a hydrogen atom, an acetyl group or an ethoxycarbonyl group;

$R^4$ represents a methyl or a t-butyl group; and $R^5$ represents a hydrogen atom or a methyl group.

20. The method of claim 5, wherein $R^1$ represents an alkyl group having from 1 to 4 carbon atoms.

21. The method of claim 5, wherein $R^2$ represents a hydrogen atom or an alkyl group having from 1 to 3 carbon atoms.

22. The method of claim 5, wherein $R^3$ represents a hydrogen atom, an aliphatic acyl group having from 1 to 4 carbon atoms, an unsubstituted benzoyl or naphthoyl group, or an alkoxycarbonyl group having from 2 to 4 carbon atoms.

23. The method of claim 5, wherein $R^4$ represents an alkyl group having from 1 to 4 carbon atoms.

24. The method of claim 5, wherein $R^5$ represents a hydrogen atom or an alkyl group having from 1 to 3 carbon atoms.

25. The method of claim 5, wherein:

$R^1$ represents an alkyl group having from 1 to 4 carbon atoms;

$R^2$ represents a hydrogen atom or an alkyl group having from 1 to 3 carbon atoms;

$R^3$ represents a hydrogen atom, an aliphatic acyl group having from 1 to 4 carbon atoms, an unsubstituted benzoyl or naphthoyl group, or an alkoxycarbonyl group having from 2 to 4 carbon atoms;

$R^4$ represents an alkyl group having from 1 to 4 carbon atoms; and $R^5$ represents a hydrogen atom or an alkyl group having from 1 to 3 carbon atoms.

26. The method of claim 5, wherein $R^3$ represents a hydrogen atom, an acetyl group, a benzoyl group or an ethoxycarbonyl group.

27. The method of claim 5, wherein:

$R^1$ represents an alkyl group having from 1 to 4 carbon atoms;

$R^2$ represents a hydrogen atom or an alkyl group having from 1 to 3 carbon atoms;

$R^3$ represents a hydrogen atom, an acetyl group, a benzoyl group or an ethoxycarbonyl group;

$R^4$ represents an alkyl group having from 1 to 4 carbon atoms; and $R^5$ represents a hydrogen atom or an alkyl group having from 1 to 3 carbon atoms.

28. The method of claim 5, wherein $R^1$ represents a methyl group.

29. The method of claim 5, wherein $R^2$ represents a hydrogen atom or a methyl group.

30. The method of claim 5, wherein $R^3$ represents a hydrogen atom, an acetyl group or an ethoxycarbonyl group.

31. The method of claim 5, wherein $R^4$ represents a methyl or a t-butyl group.

32. The method of claim 5, wherein $R^5$ represents a hydrogen atom or a methyl group.

33. The method of claim 5, wherein:

$R^1$ represents a methyl group;

$R^2$ represents a hydrogen atom or a methyl group;

$R^3$ represents a hydrogen atom, an acetyl group or an ethoxycarbonyl group;

$R^4$ represents a methyl or a t-butyl group; and $R^5$ represents a hydrogen atom or a methyl group.

34. The method of claim 1, wherein said insulin sensitizer is selected from the group consisting of 5-[4-(6-hydroxy-2,5,7,8-tetramethylchroman-2-ylmethoxy)-benzyl] thiazolidine-2,4-dione and pharmaceutically acceptable salts thereof.

35. The method of claim 1, wherein said insulin sensitizer is selected from the group consisting of 5-[4-(6-hydroxy-2-methyl-7-t-butylchroman-2-ylmethoxy)-benzyl] thiazolidine-2,4-dione and pharmaceutically acceptable salts thereof.

36. The method of claim 1, wherein said insulin sensitizer is selected from the group consisting of 5-[4-(6-hydroxy-2-ethyl-5,7,8-trimethylchroman-2-yl-methoxy)benzyl] thiazolidine-2,4-dione and pharmaceutically acceptable salts thereof.

37. The method of claim 1, wherein said insulin sensitizer is selected from the group consisting of 5-[4-(6-hydroxy-2-isobutyl-5,7,8-trimethylchroman-2-ylmethoxy)benzyl] thiazolidine-2,4-dione and pharmaceutically acceptable salts thereof.

38. The method of claim 1, wherein said insulin sensitizer is selected from the group consisting of 5-[4-(6-acetoxy-2,5,7,8-tetramethylchroman-2-ylmethoxy)-benzyl] thiazolidine-2,4-dione and pharmaceutically acceptable salts thereof.

39. The method of claim 1, wherein said insulin sensitizer is selected from the group consisting of 5-[4-(6-ethoxycarbonyloxy-2,5,7,8-tetramethylchroman-2-ylmethoxy)benzyl]thiazolidine-2,4-dione and pharmaceutically acceptable salts thereof.

40. The method of claim 1, wherein said insulin sensitizer is selected from the group consisting of 5-[6-(2-fluorobenzyloxy)-2-naphthylmethyl] thiazolidine-2,4-dione and pharmaceutically acceptable salts thereof.

41. The method of claim 1, wherein said insulin sensitizer is selected from the group consisting of 5-{4-[2-(5-ethylpyridin-2-yl)ethoxy]benzyl}thiazolidine-2,4-dione and pharmaceutically acceptable salts thereof.

42. The method of claim 1, wherein said insulin sensitizer is selected from the group consisting of 5-(2-benzyl-3,4-dihydro-2H-benzopyran-6-ylmethyl)-thiazolidine-2,4-dione and pharmaceutically acceptable salts thereof.

43. The method of claim 1, wherein said insulin sensitizer is selected from the group consisting of 5-[4-{2-[N-methyl-N-(pyridin-2-yl)amino]ethoxy}benzyl]-thiazolidine-2,4-dione and pharmaceutically acceptable salts thereof.

44. The method of claim 1, wherein said insulin sensitizer is selected from the group consisting of 5-(4-{2-[1-(4-2'-pyridylphenyl)ethylideneaminooxy]ethoxy}-benzyl) thiazolidine-2,4-dione and pharmaceutically acceptable salts thereof.

45. The method of claim 1, wherein said insulin sensitizer is selected from the group consisting of 4-{4-[2-(5-methyl-2-phenyloxazol-4-yl)ethoxy]benzyl}-isoxazolidine-3,5-dione and pharmaceutically acceptable salts thereof.

46. The method of claim 1, wherein said insulin sensitizer is selected from the group consisting of 5-{4-(5-methoxy-3-methylimidazo[4,5-b]pyridin-2-yl-methoxy) benzyl}thiazolidine-2,4-dione and pharmaceutically acceptable salts thereof.

47. The method of claim 1, wherein said insulin sensitizer is selected from the group consisting of 5-{4-(5-methoxy-3-methylimidazo[4,5-b]pyridin-2-yl-methoxy) benzyl}thiazolidine-2,4-dione and its hydrochloride.

48. The method of claim 1, wherein said insulin sensitizer is selected from the group consisting of 5-[4-(6-methoxy-1-methylbenzimidazol-2-ylmethoxy)benzyl]thiazolidine-2,4-dione and pharmaceutically acceptable salts thereof.

49. The method of claim 1, wherein said insulin sensitizer is selected from the group consisting of 5-[4-(1-methylbenzimidazol-2-ylmethoxy)benzyl]thiazolidine-2,4-dione and pharmaceutically acceptable salts thereof.

50. The method of claim 1, wherein said insulin sensitizer is selected from the group consisting of 5-[4-(5-hydroxy-1,4,6,7-tetramethylbenzimidazol-2-ylmethoxy)benzyl] thiazolidine-2,4-dione and pharmaceutically acceptable salts thereof.

51. The method of claim 1, wherein said insulin sensitizer is selected from the group consisting of 5-[4-(1-methylindolin-2-ylmethoxy)benzyl]thiazolidine-2,4-dione and pharmaceutically acceptable salts thereof.

52. The method of claim 1, wherein said insulin sensitizer is selected from the group consisting of 5-{4-[3-(5-methyl-2-phenyloxazol-4-yl)propionyl]benzyl}thiazolidine-2,4-dione and pharmaceutically acceptable salts thereof.

* * * * *